(12) United States Patent
Benowitz

(10) Patent No.: US 6,855,690 B2
(45) Date of Patent: Feb. 15, 2005

(54) METHODS AND COMPOSITIONS FOR TREATING OCULAR DISORDERS

(75) Inventor: Larry I. Benowitz, Newton, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 10/294,965

(22) Filed: Nov. 14, 2002

(65) Prior Publication Data

US 2003/0153501 A1 Aug. 14, 2003

Related U.S. Application Data

(63) Continuation-in-part of application No. 09/872,347, filed on Jun. 1, 2001.
(60) Provisional application No. 60/332,719, filed on Nov. 14, 2001, and provisional application No. 60/208,778, filed on Jun. 1, 2000.

(51) Int. Cl.[7] .......................... A61K 38/00; A61K 38/16
(52) U.S. Cl. .............................. 514/2; 514/12; 514/912; 514/913
(58) Field of Search .............................. 514/2, 12, 912, 514/913

(56) References Cited

FOREIGN PATENT DOCUMENTS

| FR | 2720069 | 11/1995 |
|---|---|---|
| WO | WO 97/03188 | 1/1997 |
| WO | WO 97/34618 | 7/1997 |
| WO | WO 00/13705 | 3/2000 |
| WO | WO 01/11086 | 2/2001 |

OTHER PUBLICATIONS

Conner, J.M., et al., 2001, "Nontropic actions of neurotrophins: Subcortical nerve growth factor gene delivery reverses age–related degeneration of primate cortical cholinergic innervation", PNAS 98 (4): 1941–1946.

Pauls, T.L., et al., 1996. "The Ca2+–binding proteins parvalbumin and oncomodulin and their genes: new structural and functional findings", Biochim. Biophys. Acta 1306: 39–54.

Kawamata, T. et al., 1997. "Intracisternal basic fibroblast growth factor enhances functional recovery and up–regulates the expression of a molecular marker of neuronal sprouting following focal cerebral infarction", PNAS 94: 8179–84.

Ritzler, J.M., et al., 1992, "The genes for the highly homologous Ca2+–binding proteins oncomodulin and parvalbumin are not linked in the human genome", Genomics 12: 567–572.

Weidner, N., et al., 2001, "Spontaneous corticospinal axonal plasticity and functional recovery after adult central nervous system injury", PNAS 98 (6): 3513–18.

Flanders, K.C., et al., 1998, "Transforming growth factor–betas in neurodegenerative disease", Progress in Neurobiology 54 (1): 71–85.

Di Iorio, P. et al., 2001, "Purine nucleosides protect injured neurons and stimulate neuronal regeneration by intracellular and membrane receptor–mediated mechanisms", Drug Development Research 52 (1–2): 303–315.

Poulsen, K.T., et al., 1994. "TGF–beta2 and TGF–beta3 are potent survival factors for midbrain dopaminergic neurons", Neuron 13 (5): 1245–52.

*Primary Examiner*—Gary Kunz
*Assistant Examiner*—Stephen Gucker
(74) *Attorney, Agent, or Firm*—Nixon Peabody LLP

(57) ABSTRACT

The present invention provides a method for treating and/or preventing damage to a retina or optic nerve in a subject comprising administering to the subject a therapeutically effective amount of oncomodulin. Preferably, the subject is a mammal, most preferably, a human. In preferred embodiments, the oncomodulin may be used in combination with mannose, a mannose derivative and/or inosine.

13 Claims, No Drawings

METHODS AND COMPOSITIONS FOR TREATING OCULAR DISORDERS

CROSS-REFERENCE TO RELATED APPLICATIONS

This application claims the benefit under 35 U.S.C §119(e) of U.S. provisional Application No. 60/332,719, filed Nov. 14, 2001 and is a Continuation-In-Part of application Ser. No. 09/872,347, filed Jun. 1, 2001, which claims the benefit under 35 U.S.C §119(e) of U.S. Provisional Application No. 60/208,778, filed Jun. 1, 2000.

BACKGROUND OF THE INVENTION

In the United States, glaucoma is the second leading cause of legal blindness overall and the leading cause of blindness in African-American individuals (Hiller, R and H. A. Kahn, (1975) Am. J. Ophthalmol 80: 62 and Kahn, H. A. and H. B. Moorhead (1973) US Public Health Service Publication NIH73-427, 120). Primary open glaucoma (POAG) is the most common form of glaucoma affecting 1–2% of the population over age forty (J. M. Tielsch et al., (1990) Arch Ophthalmol. 108: 286). Nearly 12,000 people in the United States are blinded annually by this disorder (H. B. Moorhead (1973) US Public Health Service Publication NIH73-427, 1202–4; J. M. Tielsch et al., (1990) Arch Ophthalmol. 108: 286 and J. M. Tielsch, in Transactions of the New Orleans Academy of Ophthalmology, Ball, S. F. Franklin R. M., Eds (Kugler, Amsterdam, 1993), pp61–68).

Glaucoma is a progressive disease which leads to optic nerve damage and, ultimately, total loss of vision. The causes of this disease have been the subject of extensive studies for many years, but are still not fully understood. The principal symptom of and/or risk factor for the disease is elevated intraocular pressure or ocular hypertension due to excess aqueous humor in the anterior chamber of the eye.

The causes of aqueous humor accumulation in the aniterior chamber are not fully understood. It is known that elevated intraocular pressure ("IOP") can be at least partially controlled by administering drugs which either reduce the production of aqueous humor within the eye, such as beta-blockers and carbonic anhydrase inhibitors, or increase the outflow of aqueous humor from the eye, such as miotics and sympathomimetics.

Most types of drugs conventionally used to treat glaucoma have potentially serious side effects. Miotics such as pilocarpine can cause blurring of vision and other visual side effects, which may lead either to decreased patient compliance or to termination of therapy. Systemically administered carbonic anhydrase inhibitors can also cause serious side effects such as nausea, dyspepsia, fatigue, and metabolic acidosis, which side effects can affect patient compliance and/or necessitate the termination of treatment. Another type of drug, beta-blockers, have increasingly become associated with serious pulmonary side effects attributable to their effects on beta-2 receptors in pulmonary tissue. Sympathomimetics, on the other hand, may cause tachycardia, arrhythmia and hypertension. Recently, certain prostaglandins and prostaglandin derivatives have been described in the art as being useful in reducing intraocular pressure.

While normalization of intraocular pressure can prevent further loss of sight, it cannot alone restore vision that has already been lost. The nerve cells that generate or constitute the optic nerve do, however, retain the natural ability to regenerate the axons (connecting fibers) that populate the optic nerve provided the proper growth factor is present.

There is therefore a continuing need for therapies that induce the regeneration of optic nerve fibers that have been lost thereby facilitating restoration of sight.

SUMMARY OF THE INVENTION

The present invention provides methods and composition for preventing and/or treating damage to the retina and optic nerve, including damage resulting from ischemic or hypoxic stress, excess intraocular pressure, or injury. The composition can be used specifically to treat damage associated with vascular occlusion or anterior ischemic optic neuropathy. The composition is also useful for treating damage arising from the presence of cytotoxins or neurotoxins, such as glutamate or other excitatory amino acids or peptides, excess intracellular calcium, and free radicals. In particular, the composition can be useful in treating damage associated with branch and central vein/artery occlusion, trauma, edema, angle-closure glaucoma, open-angle glaucoma, age related macular degeneration, retinitis pigmentosa, retinal detachments, damage associated with laser therapy (including photodynamic therapy), and surgical light-induced iatrogenic retinopathy.

In one embodiment, the present invention provides a method for treating and/or preventing damage to a retina or optic nerve in a subject comprising administering to the subject a therapeutically effective amount of a macrophage-derived factor or neurotrophic factor. Preferred neurotrophic factors include, for example, oncomodulin and TGF-$\beta$. Oncomodulin is most preferred. Preferably, the subject is a mammal, most preferably, a human.

In certain embodiments, the damage to the optic nerve is the result of glaucoma. In other embodiments, the damage to the retina is the result of macular degeneration.

In one embodiment, a cAMP modulator and/or an axogenic factor is further administered to the subject. The components can be used separately, but administered contemporaneously. While not wishing to be bound by a particular theory, it is believed that the cAMP modulator and axogenic factor potentiates the activity of the neurotrophic factor.

Preferably, the cAMP modulator is non-hydrolyzable cAMP analogues, forskolin, adenylate cyclase activators, macrophage-derived factors that stimulate cAMP, macrophage activators, calcium ionophores, membrane depolarization, phosphodiesterase inhibitors, specific phosphodiesterase IV inhibitors, beta2-adrenoreceptor inhibitors or vasoactive intestinal peptide.

Preferred axogenic factors include mannose (sometimes referred to as "AF-1"), mannose derivatives and inosine.

The neurotrophic factor may be administered, for example, topically to the eye of the subject or by intraocular injection.

The present invention further provides an article of manufacture comprising packaging material and a pharmaceutical agent contained within said packaging material, wherein said packaging material comprises a label which indicates said pharmaceutical may be administered, for a sufficient term at an effective dose, for treating and/or preventing damage to a retina or optic nerve together with a pharmaceutically acceptable carrier, wherein the pharmaceutical agent comprises oncomodulin.

Finally, the present invention provides a pharmaceutical kit for the treatment and/or prevention of damage to a retina or optic nerve. The kit includes the combination of:

(a) an oncomodulin;
(b) inosine and/or mannose (or mannose derivative); and
(c) a cAMP modulator.

Other aspects of the invention are disclosed infra.

DETAILED DESCRIPTION

The present invention provides methods and composition for preventing and/or treating damage to the retina and optic nerve, including damage resulting from ischemic or hypoxic stress, excess intraocular pressure, or injury. The composition can be used specifically to treat damage associated with vascular occlusion or anterior ischemic optic neuropathy. The composition is also useful for treating damage arising from the presence of cytotoxins or neurotoxins, such as glutamate or other excitatory amino acids or peptides, excess intracellular calcium, and free radicals. In particular, the composition can be useful in treating damage associated with branch and central vein/artery occlusion, trauma, edema, angle-closure glaucoma, open-angle glaucoma, age related macular degeneration, retinitis pigmentosa, retinal detachments, damage associated with laser therapy (including photodynamic therapy), and surgical light-induced iatrogenic retinopathy.

The composition of the present invention includes a macrophage-derived factor.

As used herein, the term "macrophage-derived factor" includes any factor derived from a macrophage that has the ability to produce a neurosalutary effect in a subject. Macrophage-derived factors include, but are not limited to, peptides such as oncomodulin and TGF-β. See, WO 01/091783, the disclosure of which is incorporated herein by reference.

As used herein, a "neurosalutary effect" means a response or result favorable to the health or function of a neuron, of a part of the nervous system, or of the nervous system generally. Examples of such effects include improvements in the ability of a neuron or portion of the nervous system to resist insult, to regenerate, to maintain desirable function, to grow or to survive. The phrase "producing a neurosalutary effect" includes producing or effecting such a response or improvement in function or resilience within a component of the nervous system. For example, examples of producing a neurosalutary effect would include stimulating axonal outgrowth after injury to a neuron; rendering a neuron resistant to apoptosis; rendering a neuron resistant to a toxic compound such as β-amyloid, ammonia, or other neurotoxins; reversing age-related neuronal atrophy or loss of function; or reversing age-related loss of cholinergic innervation.

As used herein, a "neurotrophic factor" or "neurotrophic compound" is one that induces a "neurosalutary effect" as defined above. Examples of preferred neurotrophic compounds include oncomodulin and TGF-β. Oncomodulin is preferred.

The term "axogenic factor" includes any factor that has the ability to stimulate axonal regeneration from a neuron. Examples of axogenic factors include AF-1 (mannose) and AF-2 as described in, for example, Schwalb et al. (1996) *Neuroscience* 72(4):901–10; Schwalb et al., id.; and U.S. Pat. No. 5,898,066, the contents of which are incorporated herein by reference. Other examples of axogenic factors include purines, such as inosine, as described in, for example, PCT application No. PCT/US98/03001, U.S. Pat. No. 6,440,455 and Benowitz et al. (1999) *Proc. Natl. Acad. Sci.* 96(23):13486–90, the contents of which are incorporated herein by reference.

A preferred axogenic factor in mannose(e.g., D-mannose or L-mannose) or a mannose derivative, e.g., aminomannose, mannose-6-phosphate (Phosporic acid mano-(3,4,5,6-tetrahydroxy-tetrahydro-pyran-2-ylmethy) ester).

A therapeutically effective amount or dosage of an axogenic factor may range from about 0.001 to 30 mg/kg body weight, with other ranges of the invention including about 0.01 to 25 mg/kg body weight, about 0.1 to 20 mg/kg body weight, about 1 to 10 mg/kg, 2 to 9 mg/kg, 3 to 8 mg/kg, 4 to 7 mg/kg, and 5 to 6 mg/kg body weight. For inosine, a non-limiting range for a therapeutically effective in vivo concentration in tissue containing the injury is 5 $\mu$M to 5 mM.

The term "cAMP modulator" includes any compound which has the ability to modulate the amount, production, concentration, activity or stability of cAMP in a cell, or to modulate the pharmacological activity of cellular cAMP. cAMP modulators may act at the level of adenylate cyclase, upstream of adenylate cyclase, or downstream of adenylate cyclase, such as at the level of cAMP itself, in the signaling pathway that leads to the production of cAMP. Cyclic AMP modulators may act inside the cell, for example at the level of a G-protein such as Gi, Go, Gq, Gs and Gt, or outside the cell, such as at the level of an extra-cellular receptor such as a G-protein coupled receptor. Cyclic AMP modulators include activators of adenylate cyclase such as forskolin; non-hydrolyzable analogues of cAMP including 8-bromo-cAMP, 8-chloro-cAMP, or dibutyryl cAMP (db-cAMP); isoprotenol; vasoactive intestinal peptide; calcium ionophores; membrane depolarization; macrophage-derived factors that stimulate cAMP; agents that stimulate macrophage activation such as zymosan or IFN-γ; phosphodiesterase inhibitors such as pentoxifylline and theophylline; specific phosphodiesterase IV (PDE IV) inhibitors; and beta 2-adrenoreceptor agonists such as salbutamol. The term cAMP modulator also includes compounds which inhibit cAMP production, function, activity or stability, such as phosphodiesterases, such as cyclic nucleotide phosphodiesterase 3B. cAMP modulators which inhibit cAMP production, function, activity or stability are known in the art and are described in, for example, Nano et al. (2000) *Pflugers Arch* 439(5):547–54, the contents of which are incorporated herein by reference.

"Phosphodiesterase IV inhibitor" refers to an agent that inhibits the activity of the enzyme phosphodiesterase IV. Examples of phosphodiesterase IV inhibitors are known in the art and include 4-arylpyrrolidinones, such as rolipram, nitraquazone, denbufylline, tibenelast,CP-80633 and quinazolinediones such as CP-77059.

"Beta-2 adrenoreceptor agonist" refers to an agent that stimulates the beta-2 adrenergic receptor. Examples of beta-2 adrenoreceptor agonists are known in the art and include salmeterol, fenoterol and isoproterenol.

The term "administering" to a subject includes dispensing, delivering or applying an active compound in a pharmaceutical formulation to a subject by any suitable route for delivery of the active compound to the desired location in the subject, including delivery by either the parenteral or oral route, intramuscular injection, subcutaneous/intradermal injection, intravenous injection, buccal administration, transdermal delivery and administration by the rectal, colonic, vaginal, intranasal or respiratory tract route.

As used herein, the language "contacting" is intended to include both in vivo or in vitro methods of bringing a compound of the invention into proximity with a neuron such that the compound can exert a neurosalutary effect on the neuron.

As used herein, the term "effective amount" includes an amount effective, at dosages and for periods of time necessary, to achieve the desired result, such as sufficient to produce a neurosalutary effect in a subject. An effective amount of an active compound as defined herein may vary according to factors such as the disease state, age, and weight of the subject, and the ability of the active compound to elicit a desired response in the subject. Dosage regimens may be adjusted to provide the optimum therapeutic response. An effective amount is also one in which any toxic or detrimental effects of the active compound are outweighed by the therapeutically beneficial effects.

The term "subject" is intended to include animals. In particular embodiments, the subject is a mammal, a human or nonhuman primate, a dog, a cat, a horse, a cow or a rodent.

The route of administration and the dosage regimen will be determined by skilled clinicians, based on factors such as the exact nature of the condition being treated, the severity of the condition, and the age and general physical condition of the patient. Specific routes of administration may include topical application (such as by eyedrops, creams or erodible formulations to be placed under the eyelid), intraocular injection into the aqueous or the vitreous humor, injection into the external layers of the eye, such as via subconjunctival injection or subtenon injection, parenteral administration or via oral routes.

The neurotrophic compound may be contained in various types of pharmaceutical compositions, in accordance with formulation techniques known to those skilled in the art. For example, the compounds may be included in tablets, capsules, solutions, suspensions, and other dosage forms adapted for oral administration; solutions and suspensions adapted for parenteral use; and solutions and suspensions adapted for topical ophthalmic, depot, or intra-ocular injection. Solutions, suspensions, and other dosage forms adapted for depot or intra-ocular injection are particularly preferred for the prevention or treatment of acute or chronic retinal or optic nerve head damage. Compositions can also be delivered according to the teachings in WO 96/05840, which is incorporated herein by reference.

The present invention is particularly directed to compositions adapted for treatment of retinal and optic nerve head tissues. The ophthalmic compositions of the present invention will include one or more neurotrophic compounds and a pharmaceutically acceptable vehicle. An axogenic factor and/or a cAMP modulator may also be included in the composition. Various types of vehicles may be used. The vehicles will generally be aqueous in nature. Aqueous solutions are generally preferred based on ease of formulation as well as a patient's ability to easily administer such compositions by means of instilling one to two drops of the solutions in the affected eyes. However, the neurotrophic compounds of the present invention may also be readily incorporated into other types of compositions, such as suspensions, viscous or semi-viscous gels, or other types of solid or semi-solid compositions. Suspensions may be preferred for neurotrophic compounds that are relatively insoluble in water. The ophthalmic compositions of the present invention may also include various other ingredients, such as buffers, preservatives, co-solvents, and viscosity building agents.

An appropriate buffer system (e.g., sodium phosphate, sodium acetate or sodium borate) may be added to prevent pH drift under storage conditions.

Ophthalmic products for topical use may be packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% weight/volume ("% w/v"). Such preparations may be packaged in dropper bottles or tubes suitable for safe administration to the eye, along with instructions for use.

When the ophthalmic compositions of the present invention are administered during intraocular surgical procedures, such as through retrobulbar or periocular injection and intraocular perfusion or injection, the use of balanced salt irrigating solutions as vehicles are most preferred. BSS Sterile Irrigating Solution and BSS Plus® Sterile Intraocular Irrigating Solution (Alcon Laboratories, Inc., Fort Worth, Tex. USA) are examples of physiologically balanced intraocular irrigating solutions. The latter type of solution is described in U.S. Pat. No. 4,550,022 (Garabedian, et al.), the entire contents of which are hereby incorporated in the present specification by reference. Retrobulbar and periocular injections are known to those skilled in the art and are described in numerous publications including, for example, *Ophthalmic Surgery: Principles of Practice*, Ed., G. L. Spaeth. W. B. Sanders Co., Philadelphia, Pa., U.S.A., (1990).

As indicated above, use of the ophthalmic compositions of the present invention to prevent or reduce damage to retinal and optic nerve head tissues, as well as to enhance functional recovery after damage to ocular tissues, is a particularly important aspect of the present invention. Ophthalmic conditions that may be treated include, but are not limited to, retinopathies (including diabetic retinopathy and retrolental fibroplasia), macular degeneration, ocular ischemia, glaucoma. Other conditions to be treated with the methods of the invention include damage associated with injuries to ophthalmic tissues, such as ischemia reperfusion injuries, photochemical injuries, and injuries associated with ocular surgery, particularly injuries to the retina or optic nerve head by exposure to light or surgical instruments. The ophthalmic compositions may also be used as an adjunct to ophthalmic surgery, such as by vitreal or subconjunctival injection following ophthalmic surgery. The compounds may be used for acute treatment of temporary conditions, or may be administered chronically, especially in the case of degenerative disease. The ophthalmic compositions may also be used prophylactically, especially prior to ocular surgery or noninvasive ophthalmic procedures or other types of surgery.

In general, the doses used for the above described purposes will vary, but will be in an effective amount to prevent, reduce or ameliorate retinal or optic nerve head tissue damage resulting from any of the above listed conditions. As used herein, the term "pharmaceutically effective amount" refers to an amount of one or more neurotrophic compounds such that treatment of a patient with that amount can be associated with a medically desirable change in ocular function, or that can prevent, reduce, or ameliorate chronic or acute retinal or optic nerve damage resulting from conditions such as trauma to the eye, ischemia or hypoxia.

The doses used for any of the above-described purposes of the neurotrophic factor will generally be from about 0.01 to about 100 milligrams per kilogram of body weight (mg/kg), administered one to four times per day. When the compositions are dosed topically, they will generally be in a concentration range of from 0.001 to about 5% w/v, with 1–2 drops administered 1–4 times per day.

There is also provided an article of manufacture comprising packaging material and a pharmaceutical agent contained within the packaging material. The packaging material comprises a label which indicates that the pharmaceutical may be administered, for a sufficient term at an effective dose, for treating and/or preventing damage to the retina and optic nerve, including damage resulting from ischemic or hypoxic stress, excess intraocular pressure, or injury, especially damage resulting from glaucoma and macular degeneration. The pharmaceutical agent comprises neurotrophic compounds of the present invention together with a pharmaceutically acceptable carrier.

As used herein, the term "pharmaceutically acceptable carrier" refers to any formulation which is safe, and provides the appropriate delivery for the desired route of administration of an effective amount of at least one compound of the present invention.

Pharmaceutical compositions (also referred to herein as "ophthalmic compositions") that include a neurotrophic factor and a pharmaceutically acceptable carrier may be packed with instructions for use of the pharmaceutical composition for treatment and/or prevention of damage to the retina and optic nerve. In one embodiment, the pharmaceutical composition may further include a cAMP modulator and/or an axogenic factor, such as AF-1, AF-2 or a purine such as inosine. The ingredients may be packaged together in the form of a kit.

All of the components, e.g., neurotrophic factor, cAMP modulator and axogenic factor, can be used separately, but administered contemporaneously, and can be given via a singular pharmaceutically acceptable dosage form for each component or combination of all the components as an immediate release or controlled release dosage form. Contemporaneously means the three agents are administered separately over time, but have a combined effect together after their individual administrations.

The invention is further illustrated by the following examples, which should not be construed as further limiting. The contents of all references, patents and published patent applications cited throughout this application are hereby incorporated by reference.

EXAMPLES

The following Examples 1 and 2 are formulations useful for intraocular, periocular or retrobulbar injection or perfusion.

Example 1

| Component | % w/v |
| --- | --- |
| Oncomodulin | 0.1 |
| Dibasic sodium phosphate | 0.2 |
| HPMC | 0.5 |
| Polysorbate 80 | 0.05 |
| Benzalkonium chloride | 0.01 |
| Sodium chloride | 0.75 |
| Edetate disodium | 0.01 |
| NaOH/HCl | q.s. to pH 7.4 |
| Purified water | q.s. to 100% |
| Cremophor EL | 10 |
| Tromethamine | 0.12 |
| Boric acid | 0.3 |
| Mannitol | 4.6 |
| Edetate disodium | 0.1 |
| Benzalkonium chloride | 0.1 |

-continued

| Component | % w/v |
| --- | --- |
| NaOH/HCl | q.s. to pH 7.4 |
| Purified water | q.s. to 100% |

Example 2

| Component | % w/v |
| --- | --- |
| Oncomodulin | 0.1 |
| Inosine | 0.1 |
| cAMP modulator | 0.1 |
| Dibasic sodium phosphate | 0.2 |
| HPMC | 0.5 |
| Polysorbate 80 | 0.05 |
| Benzalkonium chloride | 0.01 |
| Sodium chloride | 0.75 |
| Edetate disodium | 0.01 |
| NaOH/HCl | q.s. to pH 7.4 |
| Purified water | q.s. to 100% |
| Cremophor EL | 10 |
| Tromethamine | 0.12 |
| Boric acid | 0.3 |
| Mannitol | 4.6 |
| Edetate disodium | 0.1 |
| Benzalkonium chloride | 0.1 |
| NaOH/HCl | q.s. to pH 7.4 |
| Purified water | q.s. to 100% |

Example 3

A neurotrophic factor can be formulated in an ocular irrigating solution used during ophthalmic surgery to treat retinal or optic nerve head damage resulting from trauma due to injury or to prevent damages resulting from the invasive nature of the surgery. The concentration of the neurotrophic compound in the irrigating solution will range from 0.001 to 5% w/v.

A tablet formulation can be made pursuant to U.S. Pat. No. 5,049,586, incorporated herein by reference, and exemplified as following:.

| Component | % w/v |
| --- | --- |
| Neurotrophic factor | 60 |
| Magnesium oxide | 20 |
| Corn starch | 15 |
| Polyvinylpyrrolidone | 3 |
| Sodium carboxymethylcellulose | 1 |
| Magnesium sterate | 0.8 |

Those skilled in the art will recognize, or be able to ascertain using no more than routine experimentation, many equivalents to the specific embodiments of the invention described herein. Such equivalents are intended to be encompassed by the following claims.

I claim:

1. A method for treating damage to a retina or optic nerve in a subject in need of such treatment comprising administering to the subject a therapeutically effective amount of oncomodulin.

2. The method of claim 1, further comprising administering to said subject a cAMP modulator.

3. The method of claim 2, wherein said cAMP modulator is non-hydrolyzable cAMP analogues, forskolin, adenylate cyclase activators, macrophage-derived factors that stimulate cAMP, macrophage activators, calcium ionophores, membrane depolarization, phosphodiesterase inhibitors, specific phosphodiesterase IV inhibitors, beta2-adrenoreceptor inhibitors or vasoactive intestinal peptide.

4. The method of claim 1, further comprising administering mannose or a mannose derivative to said subject.

5. The method of claim 1, further comprising administering inosine to said subject.

6. The method of claim 3, wherein the cAMP modulator is forskolin.

7. The method of claim 1, wherein the damage to the optic nerve is the result of glaucoma.

8. The method of claim 1, wherein the damage to the retina is the result of macular degeneration.

9. The method of claim 1, wherein the oncomodulin is administered topically to the eye of the subject.

10. The method of claim 1, wherein the oncomodulin is administered by intraocular injection.

11. The method of claim 1, wherein the oncomodulin is administered to the subject in a pharmaceutically acceptable formulation.

12. The method of claim 1, wherein the subject is a mammal.

13. The method of claim 12, wherein the mammal is a human.

* * * * *

UNITED STATES PATENT AND TRADEMARK OFFICE
CERTIFICATE OF CORRECTION

PATENT NO. : 6,855,690 B2  
APPLICATION NO. : 10/294965  
DATED : February 15, 2005  
INVENTOR(S) : Larry I. Benowitz Page 1 of 1

It is certified that error appears in the above-identified patent and that said Letters Patent is hereby corrected as shown below:

On the Face Page of the Patent, Reference [75] Inventor: Larry I. Benowitz, Newton, MA (US) should appear as follows:

[75] Inventor: Larry I. Benowitz, Newton, MA (US)  
Yuqin Yin, Boston, MA (US)

Signed and Sealed this

Twenty-fourth Day of June, 2008

JON W. DUDAS  
*Director of the United States Patent and Trademark Office*

UNITED STATES PATENT AND TRADEMARK OFFICE
CERTIFICATE OF CORRECTION

| | | |
|---|---|---|
| PATENT NO. | : 6,855,690 B2 | Page 1 of 1 |
| APPLICATION NO. | : 10/294965 | |
| DATED | : February 15, 2005 | |
| INVENTOR(S) | : Larry I. Benowitz | |

It is certified that error appears in the above-identified patent and that said Letters Patent is hereby corrected as shown below:

In the Specification

At Column 1, Line 12, insert the following:
-- GOVERNMENT SUPPORT
This invention was made with government support under Grant no. EY005690, awarded by The National Institutes of Health. The government has certain rights in the invention. --

Signed and Sealed this
Twenty-third Day of June, 2020

Andrei Iancu
*Director of the United States Patent and Trademark Office*